United States Patent
Min et al.

(10) Patent No.: US 7,430,447 B2
(45) Date of Patent: *Sep. 30, 2008

(54) EVOKED RESPONSE AND IMPEDANCE MEASURES FOR MONITORING HEART FAILURE AND RESPIRATION

(75) Inventors: Xiaoyi Min, Thousand Oaks, CA (US); Euljoon Park, Valencia, CA (US); Malin Öhlander, Stockholm (SE)

(73) Assignee: Pacesetter, Inc., Sylmar, CA (US)

( * ) Notice: Subject to any disclaimer, the term of this patent is extended or adjusted under 35 U.S.C. 154(b) by 148 days.

This patent is subject to a terminal disclaimer.

(21) Appl. No.: 11/149,058

(22) Filed: Jun. 6, 2005

(65) Prior Publication Data

US 2006/0276848 A1 Dec. 7, 2006

(51) Int. Cl.
*A61N 1/00* (2006.01)

(52) U.S. Cl. .............................. 607/17; 607/9; 600/508

(58) Field of Classification Search .................. 607/17; 600/508, 529, 538
See application file for complete search history.

(56) References Cited

U.S. PATENT DOCUMENTS

| | | | | |
|---|---|---|---|---|
| 4,712,555 | A | 12/1987 | Thornander et al. ... | 128/419 PG |
| 4,788,980 | A | 12/1988 | Mann et al. ........... | 128/419 PG |
| 4,940,052 | A | 7/1990 | Mann et al. ........... | 128/419 PG |
| 4,944,298 | A | 7/1990 | Sholder ................ | 128/419 PG |
| 5,184,615 | A | 2/1993 | Nappholz et al. | |
| 5,466,254 | A | 11/1995 | Helland .................. | 607/123 |
| 5,507,785 | A * | 4/1996 | Deno ..................... | 607/24 |
| 5,578,064 | A * | 11/1996 | Prutchi .................. | 607/19 |
| 5,683,427 | A * | 11/1997 | Ekwall .................. | 607/11 |
| 5,957,861 | A * | 9/1999 | Combs et al. .......... | 600/547 |
| 6,314,323 | B1 | 11/2001 | Ekwall .................. | 607/23 |
| 6,454,719 | B1 | 9/2002 | Greenhut .............. | 600/484 |
| 6,589,188 | B1 | 7/2003 | Street et al. ........... | 600/538 |
| 6,600,949 | B1 | 7/2003 | Turcott ................. | 600/518 |
| 6,741,885 | B1 | 5/2004 | Park et al. ............. | 600/509 |
| 7,212,858 | B2 * | 5/2007 | Schaldach et al. ...... | 607/9 |
| 2001/0037067 | A1 | 11/2001 | Tchou et al. ........... | 600/483 |
| 2003/0040776 | A1 | 2/2003 | Kroll et al. ............ | 607/9 |
| 2003/0105499 | A1 | 6/2003 | Hartley et al. | |
| 2003/0153953 | A1 | 8/2003 | Park et al. ............. | 607/17 |
| 2004/0006375 | A1 | 1/2004 | Poezevera | |
| 2004/0106962 | A1 | 6/2004 | Mai et al. .............. | 607/19 |
| 2005/0039745 | A1 * | 2/2005 | Stahmann et al. ..... | 128/204.18 |

FOREIGN PATENT DOCUMENTS

| | | | |
|---|---|---|---|
| EP | 1348375 | A1 | 10/2003 |
| EP | 1348375 | B1 | 10/2003 |

OTHER PUBLICATIONS

NonFinal Office Action, mailed Jan. 23, 2008: Related U.S. Appl. No. 11/149,061.

* cited by examiner

*Primary Examiner*—Carl Layno
*Assistant Examiner*—Brian T Gedeon

(57) ABSTRACT

An exemplary method includes acquiring impedance values over one or more respiratory cycles, determining an impedance span based on the impedance values and, based at least in part on the impedance span, determining cardiac condition or respiratory condition. Another exemplary method includes acquiring IEGMs over one or more respiratory cycles, determining evoked response measure values based on the IEGMs, determining an evoked response span based on the evoked response measure values and, based at least in part on the evoked response span, determining cardiac condition or respiratory condition. Other exemplary methods, devices, systems, etc., are also disclosed.

20 Claims, 15 Drawing Sheets

Exemplary Method 1200

Exemplary Method 1300

EVOKED RESPONSE AND IMPEDANCE MEASURES FOR MONITORING HEART FAILURE AND RESPIRATION

RELATED APPLICATIONS

This application is related to copending U.S. Patent Applications: 1) Ser. No. 11/149,061, filed concurrently herewith, titled "Evoked Response and Impedance Measures for Monitoring Heart Failure and Respiration"; 2) Ser. No. 10/968,730, filed Oct. 18, 2004, titled "Tiered Therapy for Respiratory Oscillations Characteristic of Cheyne-Stokes Respiration", which is a continuation-in-part of U.S. patent application Ser. No. 10/765,624, filed Jan. 26, 2004, titled "Termination of Respiratory Oscillations Characteristic of Cheyne-Stokes Respiration"; 3) Ser. No. 10/765,625, filed Jan. 26, 2004, titled "Augmenting Hypoventilation"; and 4) Ser. No. 10/812,799, filed Mar. 29, 2004, titled Stimulation of Diaphragm Activation and/or Vagal Activation.

TECHNICAL FIELD

Exemplary methods, devices, systems, etc., presented herein generally relate to use of evoked response and impedance measures to monitor patient condition.

BACKGROUND

Many heart failure patients also suffer from respiratory disorders. Respiratory disorders common in heart failure patients include apnea and hypopnea, which may cycle, as characteristic of Cheyne-Stokes respiration (CSR). Apnea and CSR burden the heart with transient episodes of hypoxia and surges in sympathetic tone, which can exacerbate heart failure. Thus, a need exists for therapies to break or terminate apnea or CSR. However, diagnosis of an abnormal respiratory pattern should occur prior to implementation of such therapies.

As described herein, various exemplary methods, devices, systems, etc., detect respiratory issues using an evoked response measure and an impedance measure. In various situations, the evoked response measure or the impedance measure may indicate whether heart failure has improved or worsened. In turn, such diagnosis or information may be used to adjust therapy delivered, for example, by an implantable stimulation device.

SUMMARY

An exemplary method includes acquiring impedance values over one or more respiratory cycles, determining an impedance span based on the impedance values and, based at least in part on the impedance span, determining cardiac condition or respiratory condition. Another exemplary method includes acquiring IEGMs over one or more respiratory cycles, determining evoked response measure values based on the IEGMs, determining an evoked response span based on the evoked response measure values and, based at least in part on the evoked response span, determining cardiac condition or respiratory condition. Other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims.

Overview

As mentioned in the background section, various exemplary methods, devices, systems, etc., disclosed herein aim to detect respiratory issues using an evoked response measure or an impedance measure. Further, such measures may indicate heart condition. Yet further, selection of therapy or adjustment to therapy may rely on an evoked response measure or an impedance measure.

An evoked response measure, as described in more detail below, pertains to any of a variety of characteristics of an evoked response signal as evidenced in an intracardiac electrogram (IEGM). An impedance measure, as described in more detail, pertains to any of a variety of characteristics of an intra-thoracic impedance signal, typically capable of varying with respect to changes in tidal volume.

Where an exemplary methods, device, system, etc., includes artificial diaphragm activation, such activation may be achieved via phrenic nerve stimulation, diaphragm stimulation and/or other tissue stimulation. Artificial diaphragm activation can augment and/or act as a replacement to intrinsic means of diaphragm activation.

An exemplary stimulation device is described below followed by a discussion of various exemplary mechanisms that aim to detect a change in heart condition or a change in respiration. Various exemplary mechanisms aim to select or adjust therapy in response to such changes. The aforementioned exemplary stimulation device (described in more detail below) is optionally used to implement such exemplary tiered therapy methods.

Exemplary Stimulation Device

The techniques described below are intended to be implemented in connection with any stimulation device that is configured or configurable to stimulate nerves, stimulate muscle tissue and/or stimulate and/or shock a patient's heart (e.g., myocardial muscle tissue).

Figure 1:
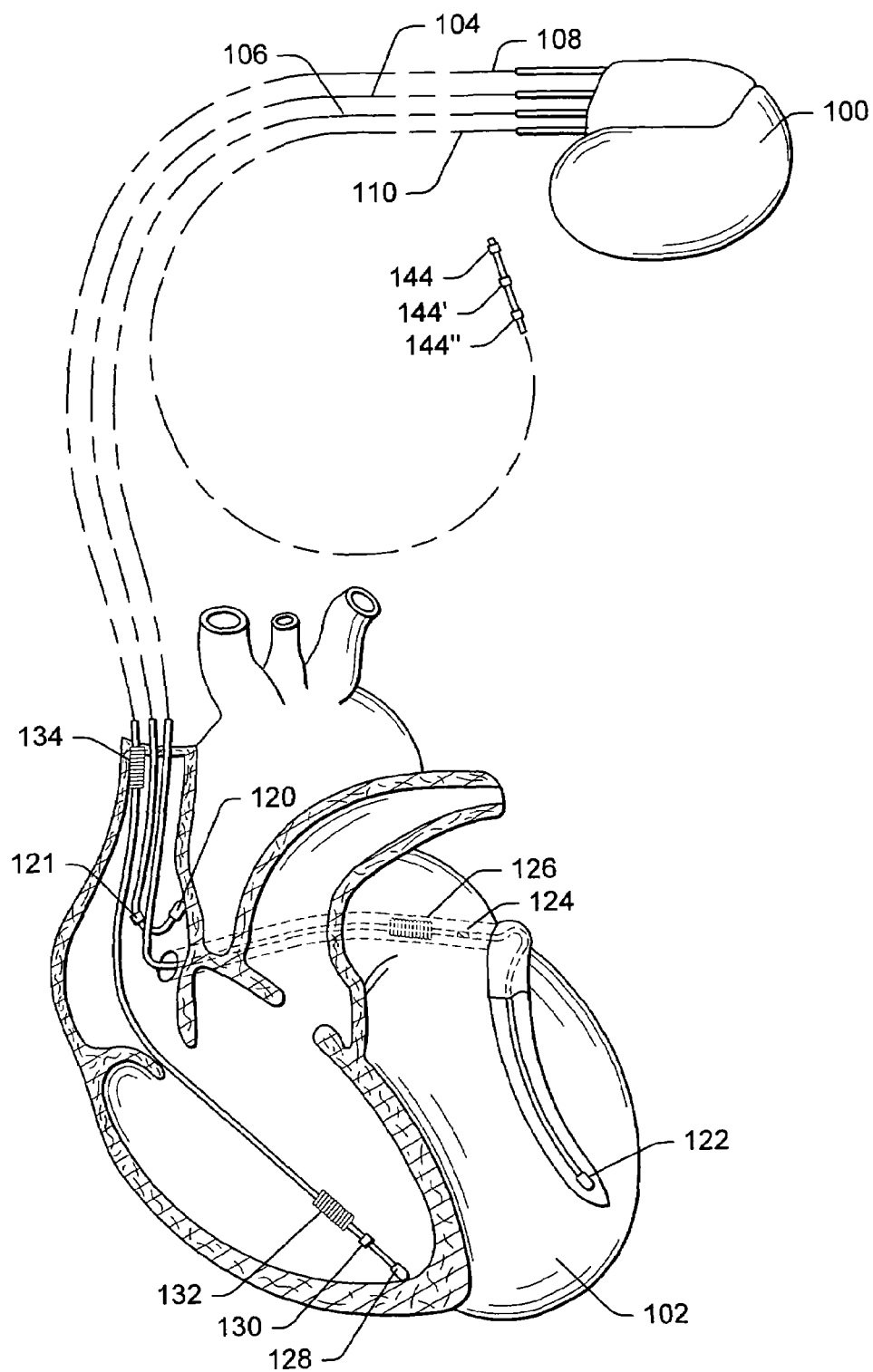
FIG. 1 is a simplified diagram illustrating an exemplary implantable stimulation device in electrical communication with at least three leads implanted into a patient's heart and at least one other lead for delivering stimulation and/or shock therapy. Exemplary devices may have lesser leads as well.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves (e.g., autonomic nerves, phrenic nerves, etc.) and/or muscle tissue other than myocardial tissue. In addition, the device 100 includes a fourth lead 110 having, in this implementation, three electrodes 144, 144', 144" suitable for stimulation of nerves (e.g., autonomic nerves, phrenic nerves, etc.) and/or muscle and/or detection of other physiologic signals that may be used by the implanted system to modify stimulation parameters. The lead 110 may be positioned in and/or near a patient's heart, near a nerve (e.g., an autonomic nerve, a phrenic nerve, etc.) or near muscle tissue other than myocardial tissue within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of nerves and/or muscle tissue.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves, other nerves and/or tissue. Such a lead may include cardiac pacing, nerve and/or muscle stimulation functionality and may further include bifurcations or legs. For example, an exemplary coronary sinus lead includes pacing electrodes capable of delivering pacing pulses to a patient's left ventricle and at least one electrode capable of stimulating a nerve (e.g., autonomic nerve, a phrenic nerve, etc.) and/or other tissue.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating a nerve and/or other tissue; such an electrode may be positioned on the lead or a bifurcation or leg of the lead. For example, an exemplary right ventricular lead includes pacing electrodes capable of delivering pacing pulses to a patient's left ventricle and at least one electrode capable of stimulating a nerve (e.g., autonomic nerve, a phrenic nerve, etc.) and/or other tissue.

Figure 2:
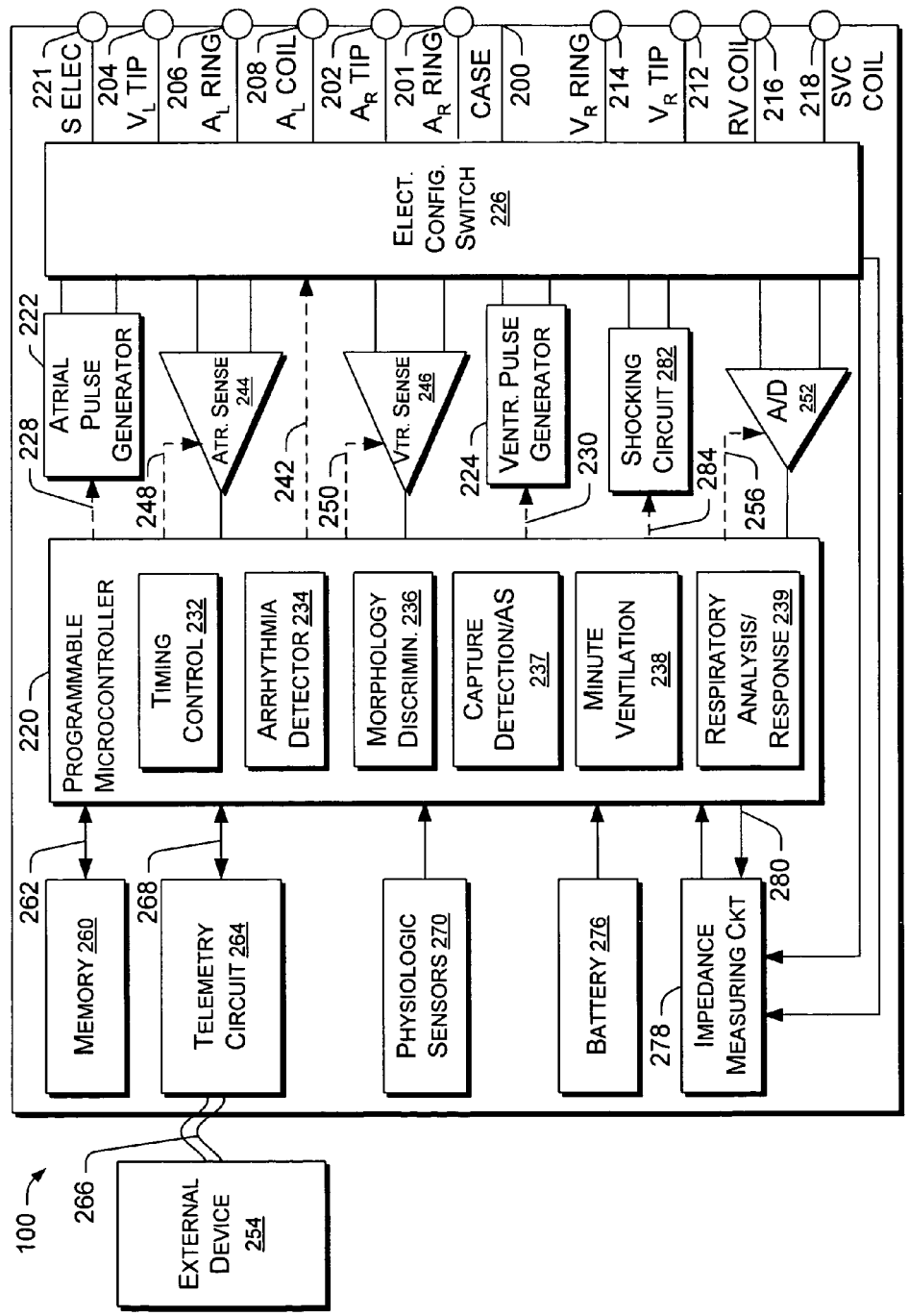
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to measure position and/or movement.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to nerves (e.g., autonomic nerves, phrenic nerves, etc.) and/or muscle tissues. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation and/or treating respiratory issues via cardiac, nerve and/or muscle stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable nerve and/or muscle stimulation electrodes is also possible via these and/or other terminals (e.g., via a stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable nerve and/or muscle stimulation electrodes is also possible via these and/or other terminals (e.g., via the stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to nerves and/or other muscle tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes, for example, an arrhythmia detector 234, a morphology discrimination module 236, a capture detection and/or autosensitivity module 237, a minute ventilation (MV) response module 238 and a respiratory analysis and/or response module 239. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture. The sensing circuits 244, 246, via switches, etc., may also be used to sense information related to respiration (e.g., chest movement monitoring, etc.).

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Nerve, muscle and/or cardiac signals are also optionally applied to inputs of an analog-to-digital (A/D) data acquisition system 252. The data acquisition system 252 is, for example, configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve and/or muscle stimulation lead through the switch 226 to sample signals across any of desired electrode (e.g., unipolar) or electrodes (e.g., multipolar).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further includes one or more physiologic sensors 270. For example, a physiologic sensor commonly referred to as a "rate-responsive" sensor is optionally included and used to adjust pacing stimulation rate according to the exercise state of the patient. However, one or more of the physiologic sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, diurnal changes in activity (e.g., detecting sleep and wake states), etc. Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that the one or more physiologic sensors 270 may also be external to the stimulation device 100, yet still be implanted within or carried by the patient.

In particular, the one or more physiologic sensors 270 optionally include a position and/or movement sensor mounted within the housing 200 of the stimulation device 100 to detect movement in the patient's position or the patient's position. Such a sensor may operate in conjunction with a position and/or movement analysis module (e.g., executable in conjunction with the microcontroller 220). The position and/or movement sensor may be implemented in many ways. In one particular implementation, the position sensor is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

Further, depending on position of the implanted device and such a movement sensor, the sensor may measure or monitor chest movement indicative of respiratory characteristics. For example, for a typical implant in the upper chest, upon inspiration, the upper chest expands thereby causing the implanted device to move. Accordingly, upon expiration, the contraction of the upper chest causes the device to move again. Such a movement sensor may sense information capable of distinguishing whether a patient is horizontal, vertical, etc.

While respiratory information may be obtained via the one or more physiologic sensors 270, the aforementioned minute ventilation (MV) sensor 238 may sense respiratory information related to minute ventilation, which is defined as the total volume of air that moves in and out of a patient's lungs in a minute. A typical MV sensor uses thoracic impedance, which is a measure of impedance across the chest cavity wherein lungs filled with air have higher impedance than empty lungs. Thus, upon inhalation, impedance increases; whereas upon exhalation, impedance decreases. Of course, a thoracic impedance may be used to determine tidal volume or measures other than minute ventilation.

With respect to impedance measurement electrode configurations, a right ventricular tip electrode and case electrode may provide current while a right ventricular ring electrode and case electrode may allow for potential sensing. Of course, other configurations and/or arrangements may be used to acquire measurements over other paths (e.g., a superior-inferior path and a left-right path, etc.). Multiple measurements may be used wherein each measurement has a corresponding path.

Direct measurement of phrenic nerve activity may be achieved using a cuff or other suitable electrode appropriately positioned in relationship to a phrenic nerve. For example, a cuff electrode substantially surrounding the right phrenic nerve in the thoracic cavity can detect signals indicative of intrinsic respiratory drive (at least to the right hemidiaphragm). Such signals are typically of amplitude measured in microvolts (e.g., less than approximately 30 microvolts). Sensing may be coordinated with other events, whether natural event or events related to some form of stimulation therapy. As discussed herein, some degree of synchronization may occur between calling for and/or delivering stimulation for diaphragm activation and sensing of neural activity and/or other indicators of respiration and, in particular, inspiration.

While respiratory characteristics are optionally measured with a signal such as a thoracic impedance signal, alternatively or in addition to, central respiratory drive is optionally determined via sensing of phrenic nerve activity. In one example, phrenic nerve (e.g., right and/or left phrenic nerve) activity is sensed using one or more electrodes on or proximate to the phrenic nerve. In another example, diaphragmatic myopotentials are sensed (e.g., EMG, etc.) using one or more electrodes on or proximate to the diaphragm. Plethysmography may be used in measuring any of a variety of variables that related to respiration.

Other means for detection include measuring the intrathoracic pressure associated with respiration or from stress and/or strain gauges measuring changes in the dimensions of the thoracic cavity including the lungs. Respiratory information may also be inferred by sensing information that relates to mechanisms altered by respiration. For example, body chemistry varies in response to respiration. Hence, chemical parameters such as tissue or blood pH, $PCO_2$, $O_2$, $PO_2$ may be sensed and either used to infer, confirm and/or augment other respiratory information.

Signals generated by the one or more physiologic sensors 270 and/or the MV sensor 238 or impedance sensor are optionally processed by the microcontroller 220 in determining whether to apply one or more therapies.

More specifically, with respect to a movement sensor, the microcontroller 220 may receive a signal from an accelerometer-based sensor that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke an orthostatic compensator to apply a prescribed stimulation therapy, especially at the onset. If the patient is traversing downstairs, the device might decrease a pacing rate or perhaps invoke the MV response module to control one or more therapies during the descent. The MV response module may provide information to be used in determining a suitable pacing rate by, for example, measuring the thoracic impedance from the MV sensor 238, computing the current MV, and comparing that with a long-term average of MV. As described herein, MV information and/or other sensed information may be used to determine an appropriate respiratory therapy.

The microcontroller 220 can also monitor one or more of the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke, for example, an orthostatic compensator to apply cardiac pacing therapy for treating orthostatic hypotension. Other uses are described in more detail below.

While a two-axis accelerometer may adequately detect tilt with respect to acceleration of gravity, the exemplary stimulation device 100 may also or alternatively be equipped with a GMR (giant magnetoresistance) sensor and circuitry that detects the earth's magnetic fields. Such a GMR sensor and circuitry may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of an accelerometer-based sensor might change by 90°, but the sensor signals may be calibrated as to the true vertical direction based on the output of a GMR sensor and circuitry.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration rate and/or tidal volume; measuring thoracic or other impedances for determining shock or other thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within or proximate to the chest cavity. Various exemplary methods described below rely on impedance measurements to determine lung inflation and/or optionally inspiratory vagal excitation, which can inhibit excitatory signals to various muscles (e.g., diaphragm, external intercostals, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the device 100 of FIGS. 1 and 2 has features suitable to call for and/or deliver appropriate diaphragm activation. With respect to calling for diaphragm activation, the respiratory analysis module 239 may be used and with respect to delivery, any of the various pulse generators, electrodes, etc., may be used. The respiratory analysis module 239 may also make determinations as to changes in heart condition (e.g., heart failure) or provide other functionality to aid in the implementation of various exemplary methods described herein.

In general, diaphragm activation involves direct or indirect phrenic nerve stimulation, transvenous phrenic nerve stimulation and/or direct or indirect diaphragm muscle stimulation.

Direct phrenic nerve stimulation uses one or more electrodes or poles (e.g., magnetic stimulation) in close proximity (e.g., typically in contact with) to a phrenic nerve. Such electrodes or poles may be positioned in the cervical region or other regions of the phrenic nerves which may be superior to the heart, proximate to the heart and/or inferior to the heart, noting that such positioning and/or stimulating may consider risk of parasitic or inadvertent cardiac activation.

Transvenous phrenic nerve stimulation involves positioning one or more electrode or pole in a vessel proximate to a phrenic nerve. For example, the right phrenic nerve runs along the intimal tissue of the superior vena cava and the left phrenic nerve runs near the innominate vein. In general, stimulation energy and power for tranvenous stimulation exceeds that of direct phrenic nerve stimulation. The diaphragm is segmented into approximately two hemidiaphragms; thus, stimulation of a right phrenic nerve may act to activate primarily the right hemidiaphragm while stimulation of a left phrenic nerve may act to activate primarily the left hemidiaphragm. Various studies indicate that an adequate level of respiration may be achieved via activation of a single hemidiaphragm. As described herein, diaphragm activation may involve right and/or left hemidiaphragm activation.

Stimulation of the diaphragm from one or more electrodes or poles positioned proximate to or in the diaphragm may achieve adequate respiration for various purposes disclosed herein. In one example, a pair of electrodes is positioned intramuscularly proximate to the region where a phrenic nerve innervates a hemidiaphragm. In this example, stimulation delivered via the pair of electrodes acts to cause diaphragm activation via nerve and/or muscle excitation. Various studies indicate that inferior placement or positioning of electrodes in or on the diaphragm is suitable to achieve diaphragm activation. Of course, other arrangements may be used where appropriate. Further, an implantable device capable of delivering stimulation for diaphragm activation may be placed subcutaneously in or near the abdomen in a manner that is less invasive than that associated with a pectoral pocket implant.

Figure 3:
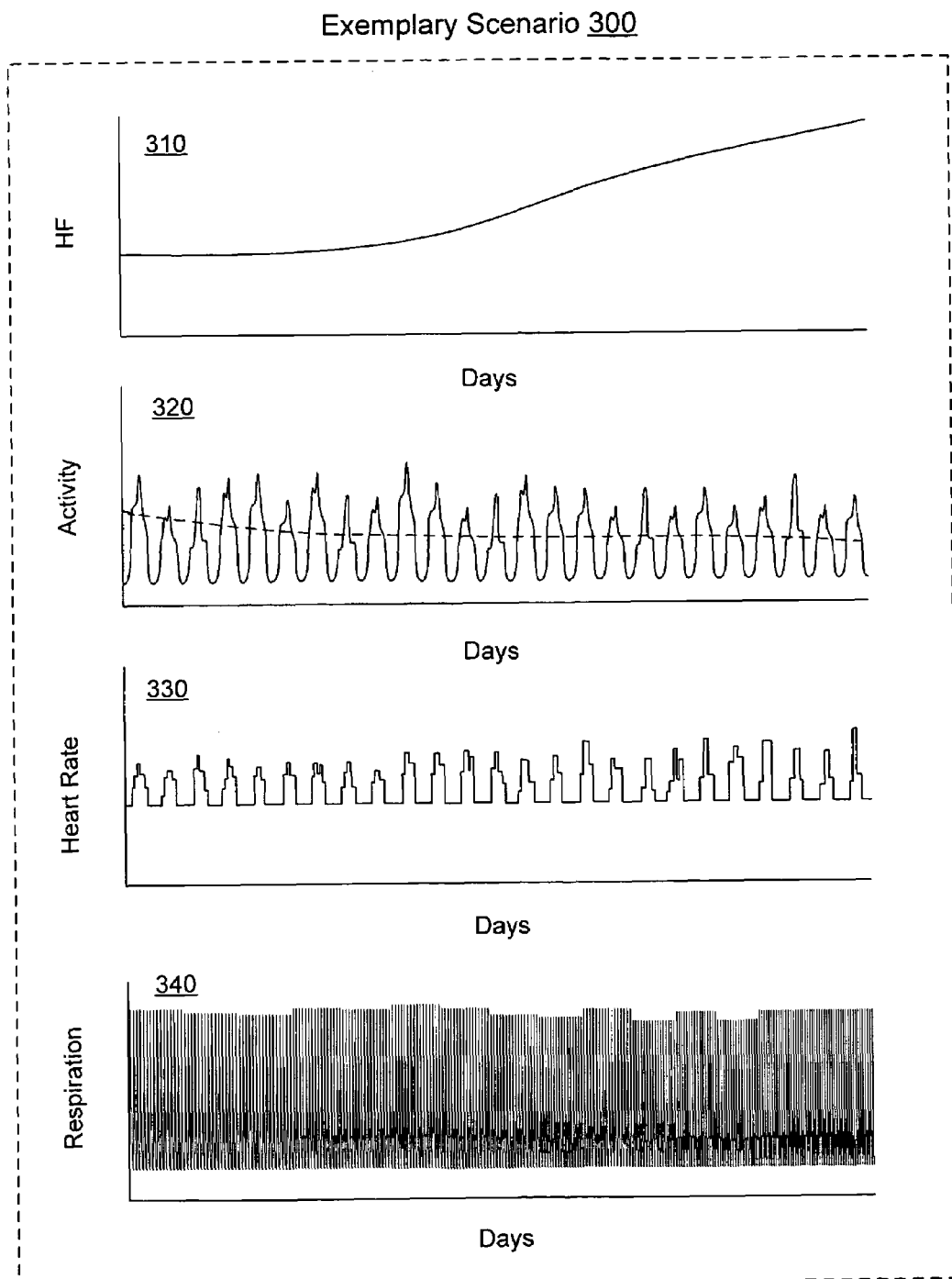
FIG. 3 is a series of plots corresponding to an exemplary scenario where heart failure worsens over a period of days.

FIG. 3 shows an exemplary scenario 300 where changes in physiology occur over a time period of days. A plot 310 of a heart failure indicator versus time indicates a worsening of heart failure over a period of days. A plot 320 of patient activity versus time indicates a slight decline in patient activity over the same period. As already mentioned, a pacing device may adjust heart rate based on patient activity. A plot 330 of heart rate versus time indicates heart rate variations, which may be based at least in part on patient activity. In general, a daily minimum in patient activity occurs sometime during sleep and, consequently, heart rate may also exhibit a daily minimum during sleep. For example, a base rate may be implemented during periods of low patient activity. A plot 340 of respiration versus time indicates that many respiration cycles occur each day. Variations in respiration, for example, tidal volume, may occur daily or over a longer period of time. The main purpose of the plot 340 is to demonstrate that the frequency of respiration, while less than beat frequency of the heart, exceeds frequency of patient activity (plot 320) or heart rate (plot 330). Overall, the exemplary scenario 300 aims to illustrate changes in patient activity, heart rate and/or respiration that may occur as heart condition worsens over a period of days.

Figure 4:
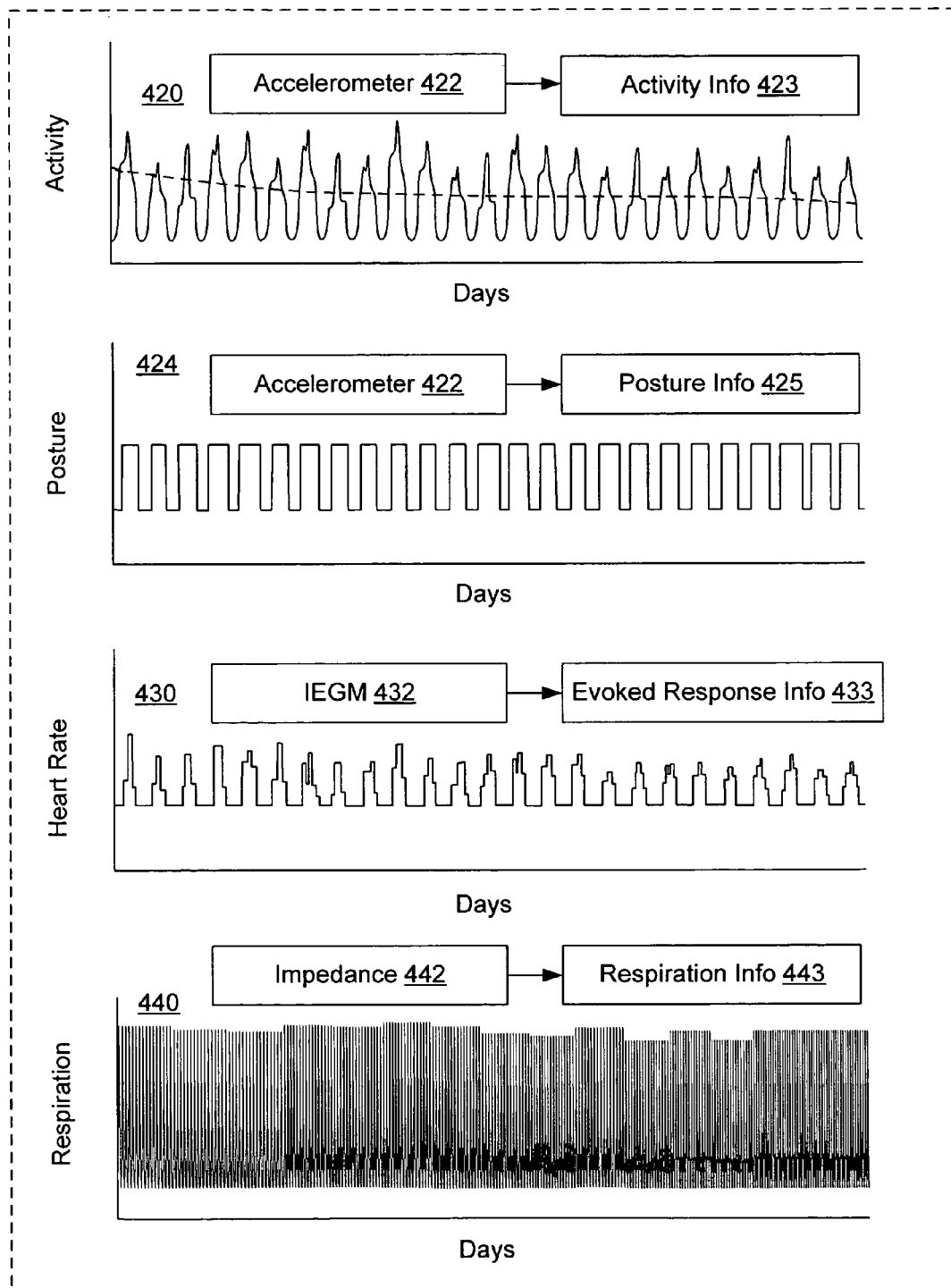
FIG. 4 is a series of plots corresponding to an exemplary scenario where patient activity or posture, heart rate and respiration are monitored over a period of days.

FIG. 4 shows an exemplary scenario 400 where various parameters are associated with various measurement blocks. A plot 420 of patient activity versus time is associated with an accelerometer block 422 that can provide activity information 423. A plot 424 of patient posture versus time is associated with the accelerometer block 422 that can provide posture information 425. Thus, an accelerometer may provide activity and posture information. Information from such a sensor may be used in conjunction with other information. For example, time may be used to distinguish night activity from day activity and, in turn, therapy may differ based on whether an activity level occurs during the night or during the day.

A plot 430 of heart rate versus time is associated with an intracardiac electrogram (IEGM) block 432 that can provide evoked response information 433. The evoked response information 433 may be used to ensure proper pacing threshold (i.e., autocapture, etc.) and may be capable of determining characteristics of an evoked response based on an IEGM. A plot 440 of patient respiration versus time is associated with an impedance block 442 that can provide respiration information 443. The impedance block 442 may be capable of impedance measurements using one or more electrode configurations and the impedance block 442 may be capable of providing information other than respiration information as well.

While a circuit for IEGM acquisition may provide evoked response information and a circuit for impedance acquisition may provide respiration information, patient posture may alter an IEGM or impedance and thereby obscure underlying changes due to disease related physiology. Various exemplary methods, devices, systems, etc., reduce effects due to posture and thereby allow for detection of conditions that may affect IEGMs or impedance. As described herein, posture effects may be reduced by using span (i.e., differences between measures) or other techniques.

Figure 5:
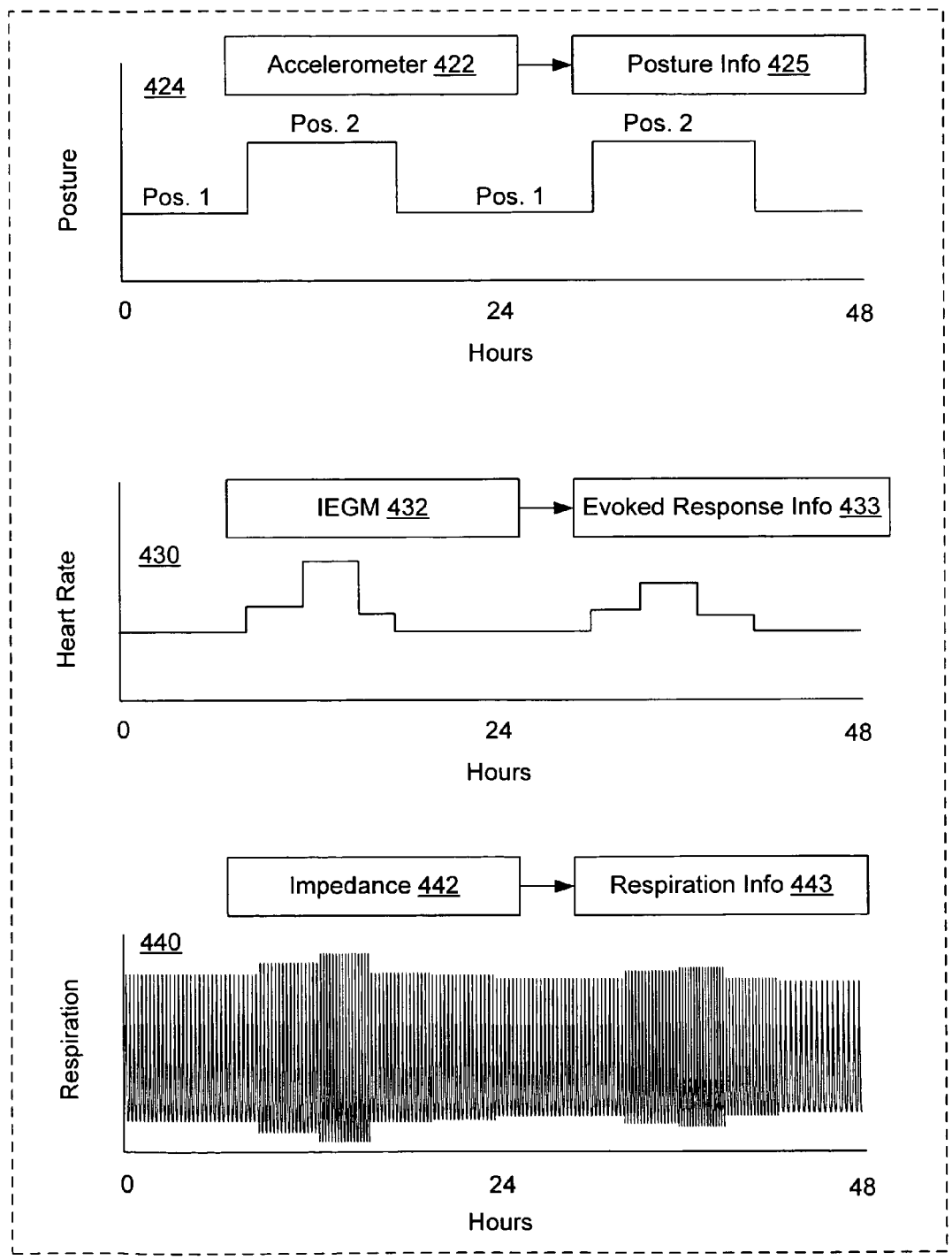
FIG. 5 is a series of plots that correspond to the exemplary scenario of FIG. 4, however, over a period of hours.

FIG. 5 shows an exemplary scenario 404, which is a portion of the scenario 400 for a period of about 48 hours. The plot 424 of posture versus time indicates that the patient has an extended period of a first posture and an extended period of a second posture, for example, based on information 425 from the accelerometer 422. In this example, the first posture corresponds to supine while the second posture corresponds to prone. Of course, more than one patient position or posture may be detected or detectable depending on an implantable device's capabilities. For example, a device may detect supine, right supine, left supine, or degrees of supine (or prone). Further, as mentioned above, time or other information may be used in conjunction with activity sensor or position sensor information.

The plot 430 of heart rate versus time indicates that changes to heart rate occur several times while the patient is in the prone position. Evoked response information 433 from the IEGM block 432 may be analyzed periodically or may be continuously analyzed where an IEGM is acquired after each paced stimulus.

The plot 440 of respiration versus time is based on impedance measurements per the impedance block 442 that provide respiration information 443 and optionally other information (e.g., cardiac information, etc.). For example, intra-thoracic impedance measurements acquired by an implantable pacing device may track respiration over time. In general, during waking hours and during activity, impedance may indicate increased tidal volume, increased respiratory frequency (i.e., decreased respiratory cycle time), etc.

Figure 6:
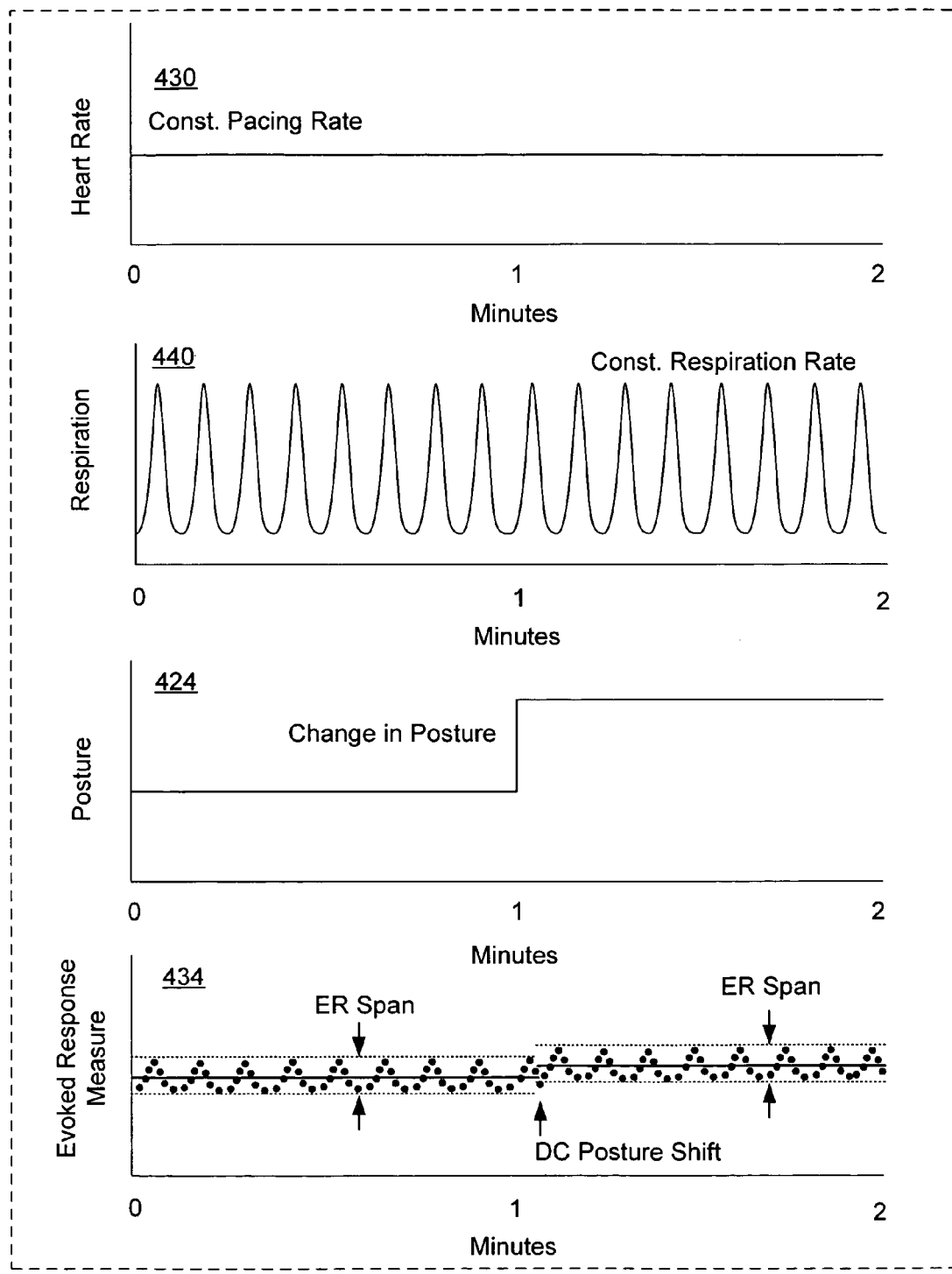
FIG. 6 is a series of plots that correspond to the exemplary scenario of FIG. 4, however, over a period of minutes.

FIG. 6 shows an exemplary scenario 408, which is a portion of the scenario 404 over a shorter period of time on the scale of minutes. The plot 430 of heart rate versus time indicates that the pacing rate is constant. The plot 440 of respiration versus time indicates that respiratory characteristics are substantially constant. The plot 424 of posture versus time indicates that the patient's posture changed at about halfway through the approximately two minute time period. A plot 434 of values of an evoked response measure versus time indicates respiration dependence and posture dependence. The respiration dependence exhibits variations due to variations in tidal volume which generates a span in the evoked response measure (ER Span). For example, the evoked response measure may be a post depolarization integral (PDI) where a value is determined on a beat-by-beat basis. An average of the values for the ER measure over one or more respiratory cycles is also shown where the change in posture causes a change in the average. However, in this example, there is no substantial change in the ER Span.

Figure 7:
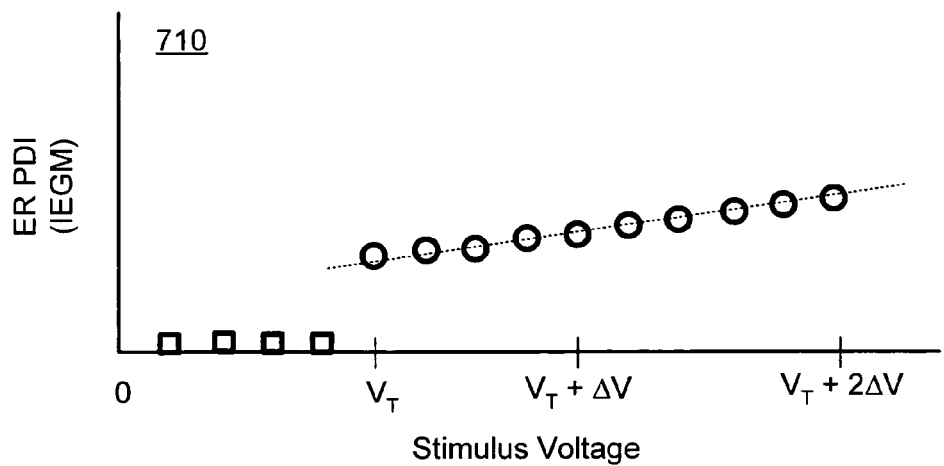
FIG. 7 is a plot of an evoked response measure versus stimulus voltage that indicates a relationship between polarization and stimulus voltage and an exemplary method that relies on the relationship between electrode polarization and stimulus voltage.
Figure 7:
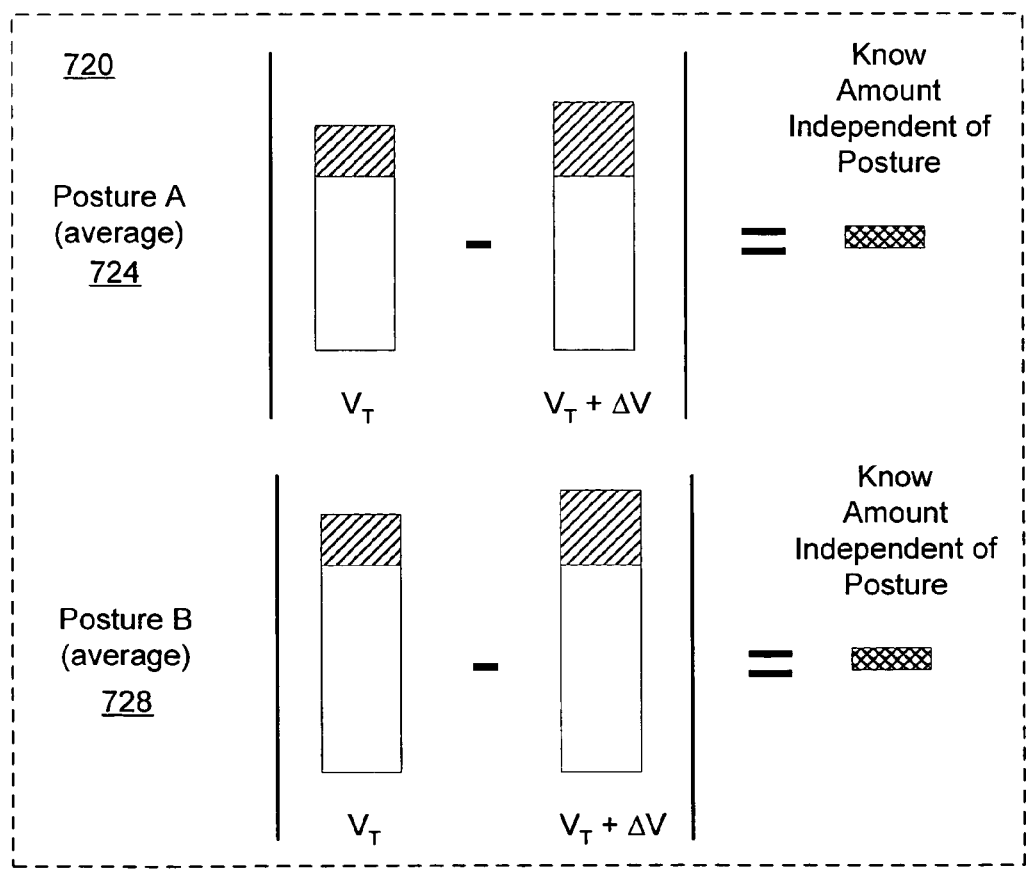

FIG. 7 shows an exemplary plot 710 of values of an evoked response measure versus stimulus voltage and an exemplary method 720 for determining a polarization contribution to the values of the evoked response measure. The plot 710 exhibits a substantially linear increase in the values of the evoked response measure (e.g., PDI) with respect to increasing stimulus voltage above a threshold voltage ($V_T$). Thus, given such a relationship, a polarization contribution to any particular value of the evoked response measure may be determined based on stimulus voltage. In instances where low polarization electrodes are used for delivery of the stimulus, the slope may be minimal. Also, in the plot 710, the values of the evoked response measure are either averaged over one or more respiratory cycles or synchronized with a certain portion of the respiratory cycle as to minimize variations in the evoked response measure during a respiratory cycle. Further, polarization information may be used as an indicator of heart condition, for example, polarization often decreases with increasing CHF. Also, in general, polarization is not affected by posture.

The exemplary method 720 includes subtracting a value of an evoked response measure for a stimulus delivered at one voltage from a value of an evoked response measure for a stimulus delivered at another voltage. Two situations are shown where one situation corresponds to a first patient posture (Posture A) 724 and the other situation corresponds to a second patient posture (Posture B) 728. As already mentioned (see, e.g., the plots 424, 434 of FIG. 6), patient posture may affect an evoked response measure. The effect may be known, unknown or ignored.

According to the situations 724, 728, if patient posture does not change from the stimulus at the first voltage (e.g., $V_T$) to the second voltage (e.g., $V_T+\Delta V$), then the difference is due primarily to polarization (shaded region of evoked response measure). In the exemplary method 720, an absolute value of the difference is noted. Importantly, a comparison between the difference for the situation 724 (Posture A) and the difference for the situation 728 (Posture B) may be made wherein any contribution due to patient posture is reduced or substantially eliminated.

Referring again to the plot 710, the evoked response measure ER PDI varies with respect to stimulus voltage for stimulus voltages greater than the threshold voltage $V_T$. The difference in ER PDI for a first supra-threshold voltage ($V_1$) and ER PDI at a second supra-threshold voltage ($V_2$) may be used to determine patient condition or appropriate therapy and referred to as a stimulus voltage related difference in an evoked response measure (e.g., $\Delta ER_V$). Such a measure may be divided by the difference in stimulus voltage (e.g., $\Delta ER_V / \Delta V$ where $\Delta V = |V_1 - V_2|$), and used to determine patient condition or appropriate therapy.

During a single respiratory cycle, typically more than one cardiac cycle occurs. Thus, the aforementioned $\Delta ER_V$ or $\Delta ER_V / \Delta V$ may be determined several times during a single respiratory cycle. In such instances, a maximum $\Delta ER_V$ or $\Delta ER_V / \Delta V$ or minimum $\Delta ER_V$ or $\Delta ER_V / \Delta V$ may be determined and compared to an average, to a value(s) from a different respiratory cycle, or other value(s). As already mentioned, ER Span is generally the difference between the maximum $\Delta ER_V$ or $\Delta ER_V/\Delta V$ and minimum $\Delta ER_V$ or $\Delta ER_V/\Delta V$. As ER Span is related to respiration, ER Span values are useful to indicate conditions related respiration while $\Delta ER_V$ and $\Delta ER_V/\Delta V$ are particularly useful to indicate cardiac condition (e.g., wall thickness, etc.).

Figure 8:
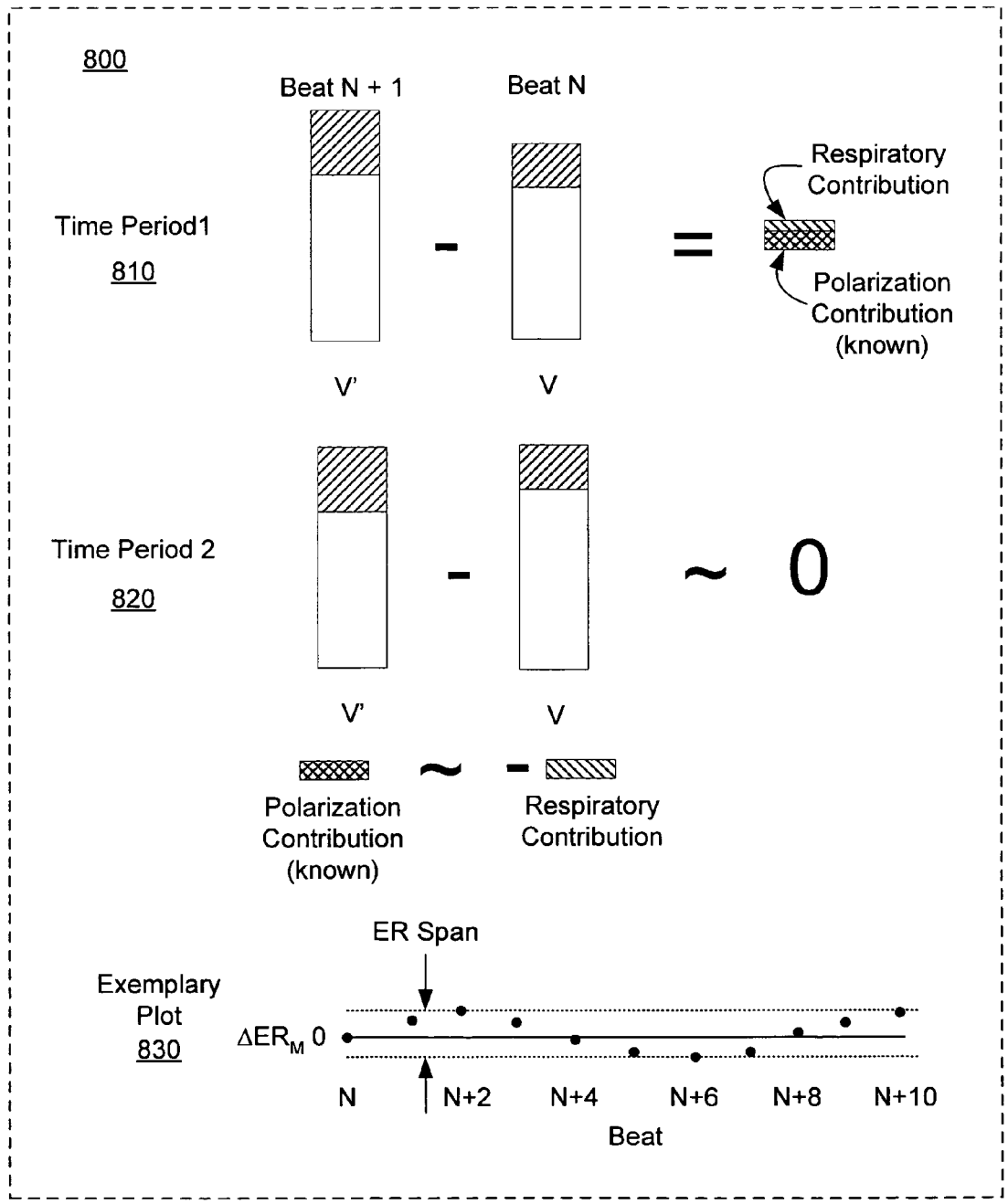
FIG. 8 is a schematic of an exemplary method that relies on an evoked response measure to detect one or more characteristics of respiration.

FIG. 8 shows an exemplary method 800 where information for an evoked response measure is acquired on a beat-by-beat basis. As explained with respect to FIG. 7, the stimulus voltage need not be constant. Thus, in a first time period (Time Period 1) 810 where posture is constant, a beat "N" caused by a stimulus voltage V (which is at threshold or supra-threshold) has an associated value of the evoked response measure and a beat "N+1" caused by a stimulus voltage V' (which is at threshold or supra-threshold) has an associated value of the evoked response measure. In general, the heart rate exceeds the respiratory rate, i.e., more than one heart beat occurs during a respiratory cycle. Thus, the beat N and the beat N+1, where consecutive, correspond to different portions of a respiratory cycle. Consequently, the values of the evoked response measure will include a respiratory contribution. Upon subtracting one value from the other, the result will include a polarization contribution and a respiratory contribution. If the polarization contribution is known a priori, then the respiratory contribution may be determined. Of course, if the information for the evoked response measure was acquired using the same stimulus voltage, then the polarization contribution would cancel upon subtracting the two values of the evoked response measure.

Values of the evoked response measure are also shown for a second time period (Time Period 2) 820 where posture is constant and where the difference is approximately zero. In this instance, the respiratory contribution is approximately equal to the opposite of the polarization contribution. In this manner, pairs of values of an evoked response measure may be used to determine respiratory characteristics where stimulus voltage polarization and patient posture contributions may be reduced. Again, for these time periods the particular postures are typically not of concern, only that the posture remained constant during each time period.

An exemplary method optionally determines a minimum value of an evoked response measure and a maximum value of the evoked response measure over one or more respiratory cycles and then compares or subtracts the two values to provide an evoked response span. For example, the plot 434 of FIG. 6 exhibits an evoked response span (ER Span). Such a parameter is optionally monitored over time to determine patient condition (e.g., respiration, heart failure, etc.). An exemplary method optionally acquires information sufficient to determine at least one value of an evoked response measure on a beat-by-beat basis for three or more respiratory cycles, averages the values of the evoked response measure and determines a standard deviation for the values. For example, if a respiratory cycle has a duration of about 8 seconds, a heart rate of 72 bpm (~0.83 seconds between beats) will yield about 10 evoked response measure values for each respiratory cycle. In this example, 30 values will be acquired over a period of about 24 seconds and it is likely that a value of the evoked response measure will substantially coincide with a transition from inhalation to exhalation and that another value of the evoked response measure will substantially coincide with a transition from exhalation to inhalation. Consequently, an evoked response difference for these two values may reflect respiration characteristics. Further, standard deviations or evoked response measure value differences over time can be used to determine patient condition.

FIG. 8 shows an exemplary plot 830 where an exemplary method determines a value of an evoked response measure ($ER_M$) at beat "N" and then uses this value to determine a change in an evoked response measure for subsequent beats "N+1" to "N+10" (e.g., $\Delta ER_M=0$, $ER_M(N)-ER_M(N+1)$, $ER_M(N)-ER_M(N+2)$, etc.). The difference between the maximum and minimum $\Delta ER_M$ values is labeled the ER Span (i.e., the same as the aforementioned ER Span because $ER_M(N)$ cancels out) and assumed to depend on respiration. However, the individual $\Delta ER_M$ values are generally more reliable because various contributions may be minimized. Should a change in posture occur during the time period (e.g., corresponding to N to N+10), an accelerometer or other appropriate circuit may indicate the change and compensate for the change or start a new comparison period (i.e., selection of a new "N").

Figure 9:
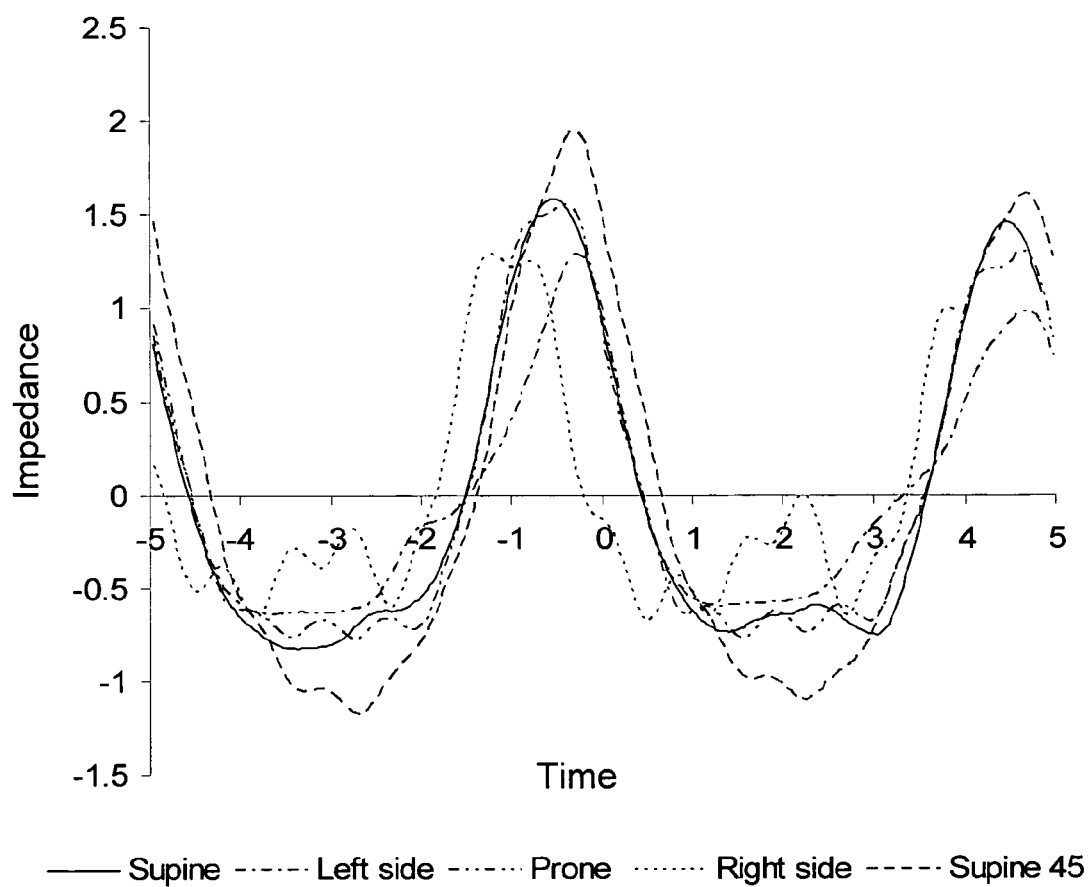
FIG. 9 is a plot of normalized impedance signal versus respiratory cycle for various patient positions.

As already mentioned, impedance measurements may be used to provide information on respiration. Further, impedance measurements may also depend on patient posture. FIG. 9 shows an exemplary plot 900 of impedance values versus time during respiratory cycles for various postures: supine, supine 45°, left side supine, right side supine and prone. In this example, impedance signals were acquired using a case and right atrial ring electrode configuration for current and a case and right atrial tip electrode for potential measurement. In practice values may be potential, impedance, resistance or in another form related to impedance. The greatest impedance value was acquired for the supine 45° posture. In comparison to this value, the maximum supine signal was 77% of the maximum supine 45° value whereas the maximum left side supine signal was about 61.7%, the right side supine signal about 62.9%, and the prone about 74.5% of the maximum supine 45° value.

In general, impedance measurements include a cardiac component and a respiratory component, which are both affected to some extent by patient posture. The cardiac component varies according to the cardiac cycle and the respiratory component varies according to the respiratory cycle, which is typically less frequent. An impedance measurement may be segregated into a cardiac component and a respiratory component using cycle information. Further, a ratio of respiratory component to cardiac component may be useful in assessing a patient's condition.

Figure 10:
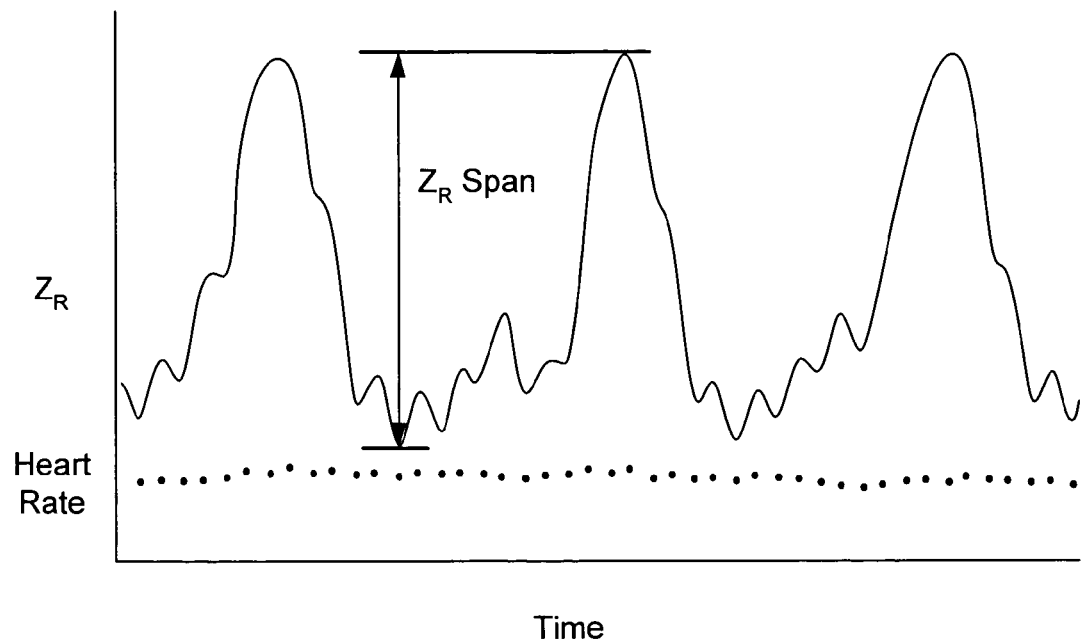
FIG. 10 is an exemplary scenario where an impedance span value is determined over one or more respiratory cycles.

FIG. 10 shows an exemplary scenario 1000 where impedance and heart rate information have been acquired over a plurality of respiratory cycles. A minimum impedance value and a maximum impedance value are detected and used to determine an impedance span ($Z_R$ Span). In instances where a baseline shift occurs (e.g., a DC shift) use of span generally acts to cancel baseline error (e.g., $Z_R$ Span=|(baseline+$Z_R$(t+$\Delta$t))-(baseline+$Z_R$(t))|) especially in instances where baseline shift or drift is not significant during a respiratory cycle.

As explained with respect to FIG. 9, impedance may vary with respect to patient position and, hence, span may vary with respect to patient position. Thus, the span determination may occur at a time when the patient is assumed to be in a particular position or when a position/posture detector (e.g., accelerometer) indicates that the patient is in a particular position, or the span determination may be associated with a position as indicated by a position/posture detector. In general, maxima and minima in a respiratory component of impedance may occur over one or more cardiac cycles and the effect of the cardiac component may cause a shift in the respiratory component. Where desired, averaging or other analysis may be used to reduce the effect of the cardiac component. In general, respiration cycles and cardiac cycles are asynchronous and hence maxima and minima in respiration component of impedance and maxima and minima in cardiac cycle component of impedance are likely to vary with respect to each other over time. Other information (e.g., time, activity, etc.) may also be used to assess an impedance span.

With respect to impedance information for different postures such as the information shown in the plot 900 of FIG. 9, Table 1, below, illustrates a data structure for storing impedance span information with respect to posture over time.

TABLE 1

Impedance span versus patient position and time

| Position | Week 1 | Week 2 | Week N − 1 | Week N |
|---|---|---|---|---|
| Supine, Left | 61.7 | 61 | 60.2 | 59.0 |
| Supine, Right | 62.9 | 61 | 60 | 58 |
| Supine ~45° | 100* | 99 | 97 | 95 |
| Supine | 77 | 75 | 74 | 72 |
| Prone | 74.5 | 74 | 73.5 | 73 |

*Used to normalize all values

According to the information in Table 1, the impedance span decreases over a period of weeks (N). In particular, the supine, right value decreases over time to become less than the supine, left value. Such information may indicate heart and/or lung ailments as the heart resides on the left side and exerts some force on the respiratory system when a patient lies on her right side. In general, it is easier to breath when lying on ones left side; however, as mentioned below, some heart failure patients cannot tolerate lying on their left side.

Often advanced heart failure patients (e.g., NYHA Class III or IV) find it difficult to breathe after several minutes of lying in a supine position because fluid cannot drain as easily from the lungs in a supine position and, indeed, may increase substantially. As fluid builds up, a patient may increase breathing frequency. Further, some patients find lying on the left side uncomfortable and detrimental to heart function as the heart experiences force from the right side of the body. Upon moving to a prone position, gravity can help drain any excess fluid out of the lungs. Ideally, patients with advanced heart failure should sleep in an inclined position (e.g., supine 45°).

Referring again to the exemplary scenario 1000, an advantage of such an exemplary method is that no zero line is needed and that it may be implemented in real time. Gain or offset may be adjusted as appropriate so that saturation of the signals does not occur and so that the center of the amplifier range coincides substantially with a long term running average.

Various exemplary methods, devices, systems, etc., may use evoked response information or impedance information to determine characteristics of respiration and then use such characteristics to monitor progression of heart failure. For example, characteristics of respiration such as frequency of breath and size of breath may indicate heart failure or a change in heart failure prior to pulmonary edema or detectable signs of pulmonary edema per traditional techniques. Early detection of pulmonary edema or detection of precursor conditions thereof can allow for proper intervention or adjustment of therapy as delivered by an implantable device.

An exemplary method monitors impedance span during sleep and compares one or more sleep-time values to a daytime average, which is optionally used as a baseline. The impedance span value or values acquired during sleep may be used to detect respiratory or other issues. For example, as described further below, Cheyne-Stokes respiration (CSR) or apnea may be detectable through use of impedance span values. CSR is known to occur in about 30% of heart failure patients.

Criteria for decision making are optionally determined at pre-discharge or office visits by posture tests through a field programmer. Other impedance values, such as minimum, maximum, mean, etc., may be used for decision making as adjuncts or as alternatives to impedance span.

Figure 11:
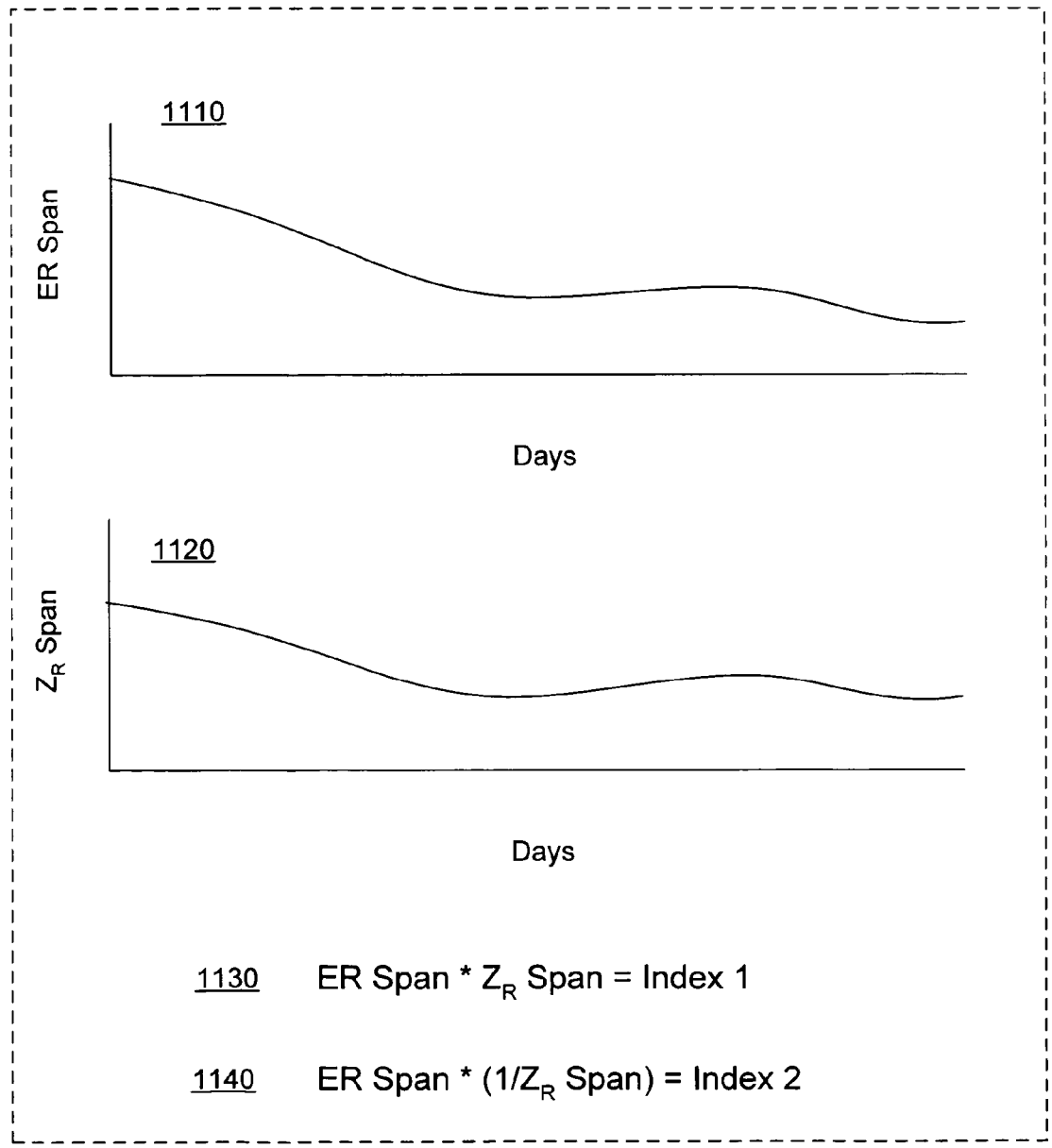
FIG. 11 is an exemplary scenario that illustrates a change in an evoked response measure span value and an impedance measure span value over time and various exemplary indexes that may rely on such values.

FIG. 11 shows an exemplary scenario 1100 that includes an evoked response measure 1110 and an impedance measure 1120 to monitor patient condition and to optionally adjust therapy. The evoked response measure, ER Span, 1110 and the impedance measure, $Z_R$ Span, are plotted versus time in days. Various indexes may be determined based on values for the evoked response measure and the impedance measure. For example, a first index 1130 corresponds to the product of an ER Span value and a $Z_R$ Span value while a second index 1140 corresponds to the ER Span value divided by the $Z_R$ Span value. In general, shallow and rapid breathing will be associated with a decreasing ER Span and a decreasing $Z_R$ Span.

Evoked response information (e.g., ER Span) or impedance information (e.g., $Z_R$ Span) may be used to monitor cardiac condition at various times. For example, information acquired during active hours (e.g., daytime) may be used to monitor CHF and compared on a day-to-day or other basis. Information acquired during sleep (e.g., nighttime) may be used to indicate whether apnea exists and, if so, to indicate whether apnea is central or obstructive. Further, information acquired during sleep may allow for determinations as to Cheyne-Stokes respiration (e.g., phase, cycle length, waxing, waning, etc.), for example, as discussed with respect to FIG. 14.

Figure 12:
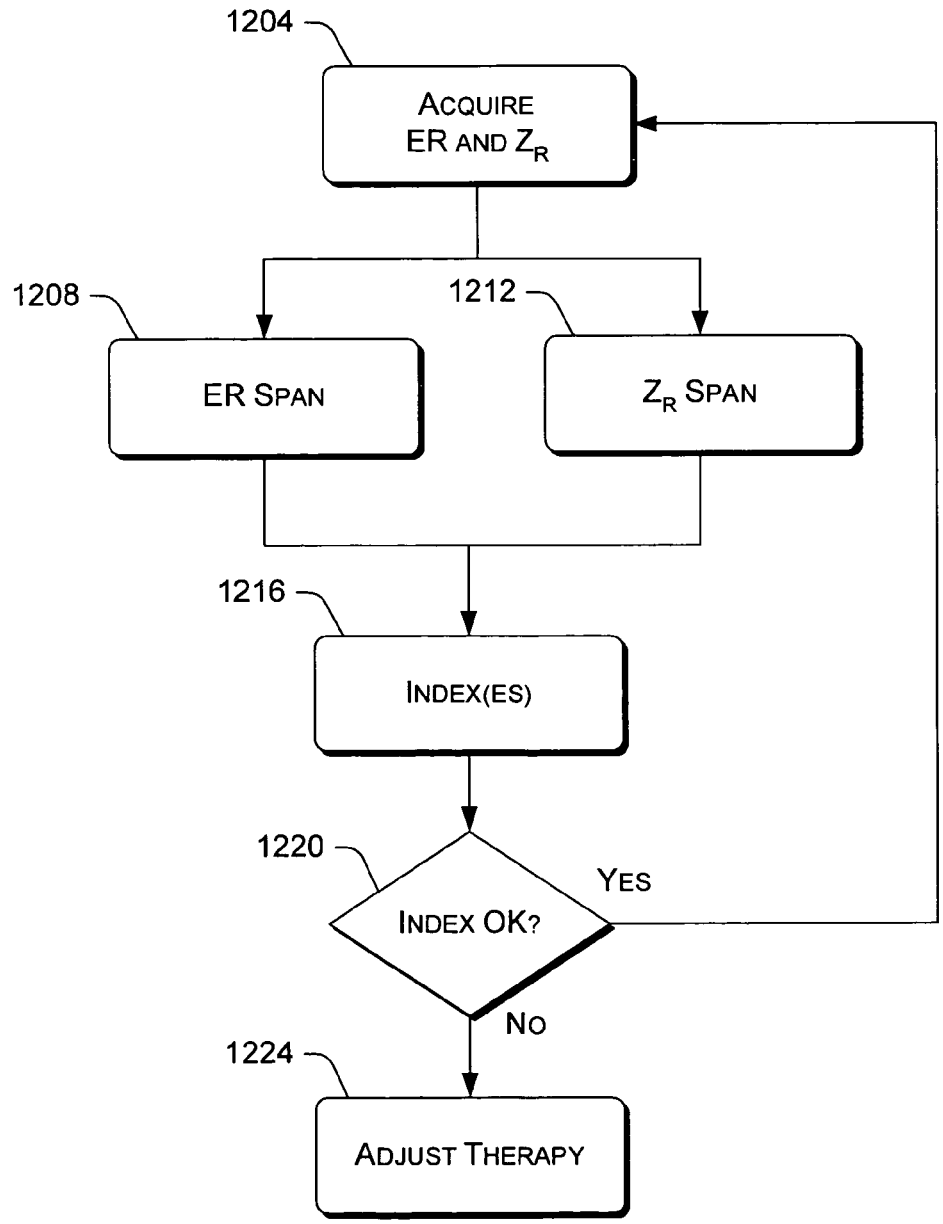
FIG. 12 is a block diagram of an exemplary method for adjusting therapy based at least in part on an evoked response span value or an impedance span value.

FIG. 12 shows an exemplary method 1200 that relies on an index to adjust therapy. In an acquisition block 1204, evoked response information and impedance information are acquired. A determination block 1208 determines an ER Span value and another determination block 1212 determines a $Z_R$ Span value. An index block 1216 then determines one or more indexes based at least in part on the ER Span value and the $Z_R$ Span value. A decision block 1220 follows that decides if the index is OK, for example, compared to historical information or other information. If the decision block 1220 decides that the index is OK, then the exemplary method 1200 continues at the acquisition block 1204. However, if the index or indexes do not compare favorably to one or more criteria, then an adjustment block 1224 adjusts the patient's therapy. The adjustment block 1224 optionally relies on the ER Span value, the $Z_R$ Span value, an index, etc., to make an appropriate adjustment to the patient's therapy.

Figure 13:
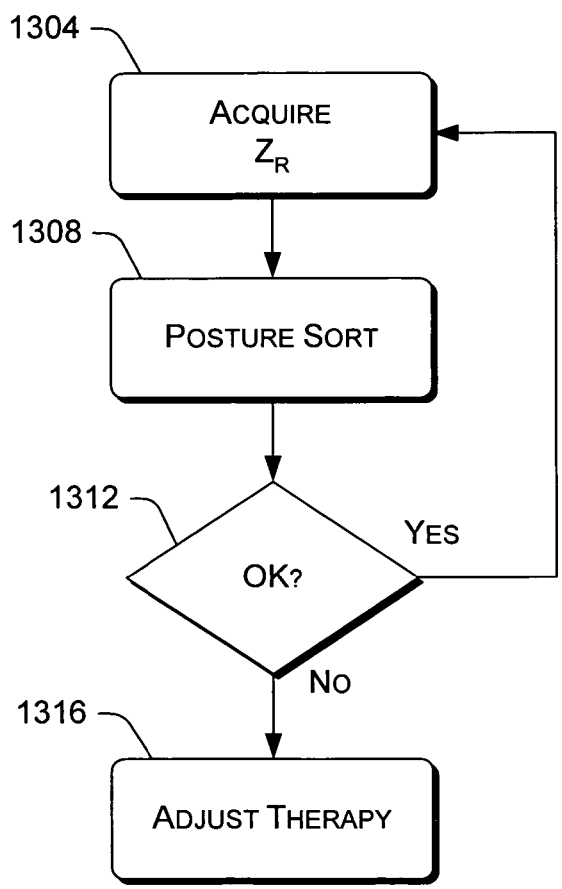
FIG. 13 is a block diagram of an exemplary method that acquires impedance information for a plurality of patient positions or postures and that optionally adjusts therapy based on such information.

FIG. 13 shows an exemplary method 1300 for adjusting patient therapy based on impedance measurements acquired at more than one patient position. In an acquisition block 1304, impedance information is acquired. A sort block 1308 follows wherein the impedance information or impedance values are sorted based on patient position at the time for which the information was acquired. A decision block 1312 follows where the sorted impedance information or values are compared to one or more criteria. If the information or values compare favorable (i.e., OK), then the exemplary method 1300 continues at the acquisition block 1304. However, if the decision block 1312 indicates that the information or values do not meet one or more of the criteria, then the method 1300 continues in an adjustment block 1316 that adjusts therapy delivered to the patient. For example, if heart failure is worsening, then a cardiac pacing therapy may be adjusted to improve cardiac function, etc.

A data structure such as that of Table 1 may be used for trend analysis. For example, recently acquired impedance information may be compared to historic information to determine patient condition or whether to adjust patient therapy.

Figure 14:
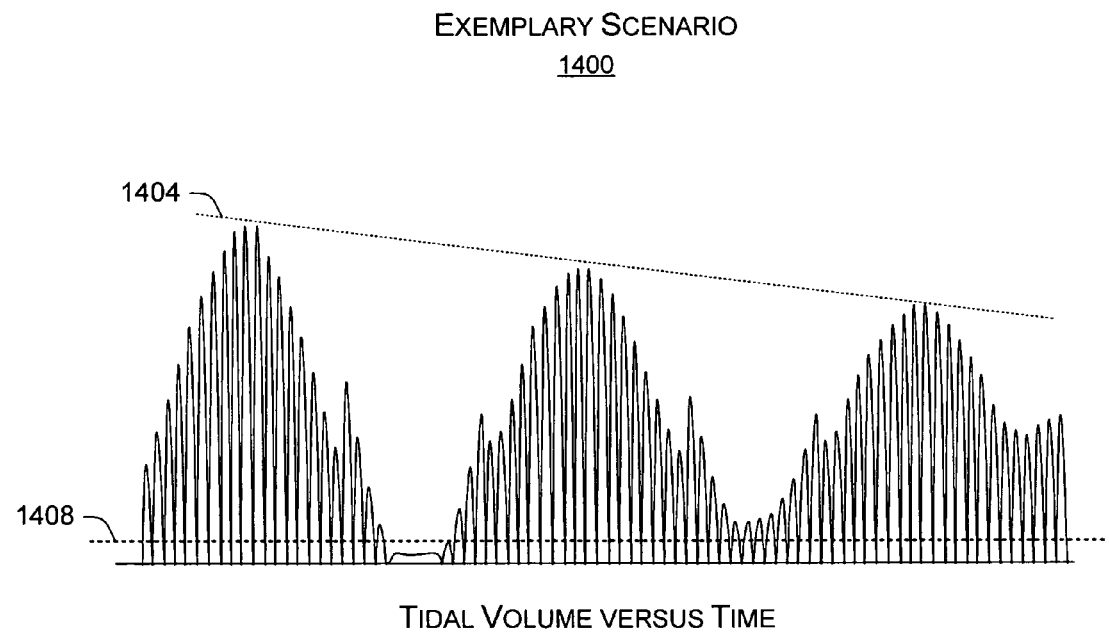
FIG. 14 is an exemplary scenario where tidal volume versus time exhibits a period of apnea and Cheyne-Stokes respiration (CSR).

FIG. 14 shows an exemplary scenario 1400 where tidal volume is plotted versus time. A line 1404 with a negative slope indicates that the tidal volume is generally decreasing over time. Another line 1408 serves as a limit to decide whether the tidal volume has decreased, for a period of time, to a level indicative of apnea. Overall, the tidal volume versus time is indicative of Cheyne-Stokes respiration (CSR) with a period of apnea. Various exemplary methods rely on evoked response information or impedance information to serve as a surrogate to tidal volume. Further, various exemplary methods optionally rely on a combination of evoked response information and impedance information to determine if a patient is experiencing respiratory issues such as CSR or apnea. Various exemplary methods optionally include distinguishing CSR phases, i.e., whether CSR is waxing or waning. In turn, therapy may be selected or adjusted based on CSR phase, duration of phase, etc.

Figure 15:
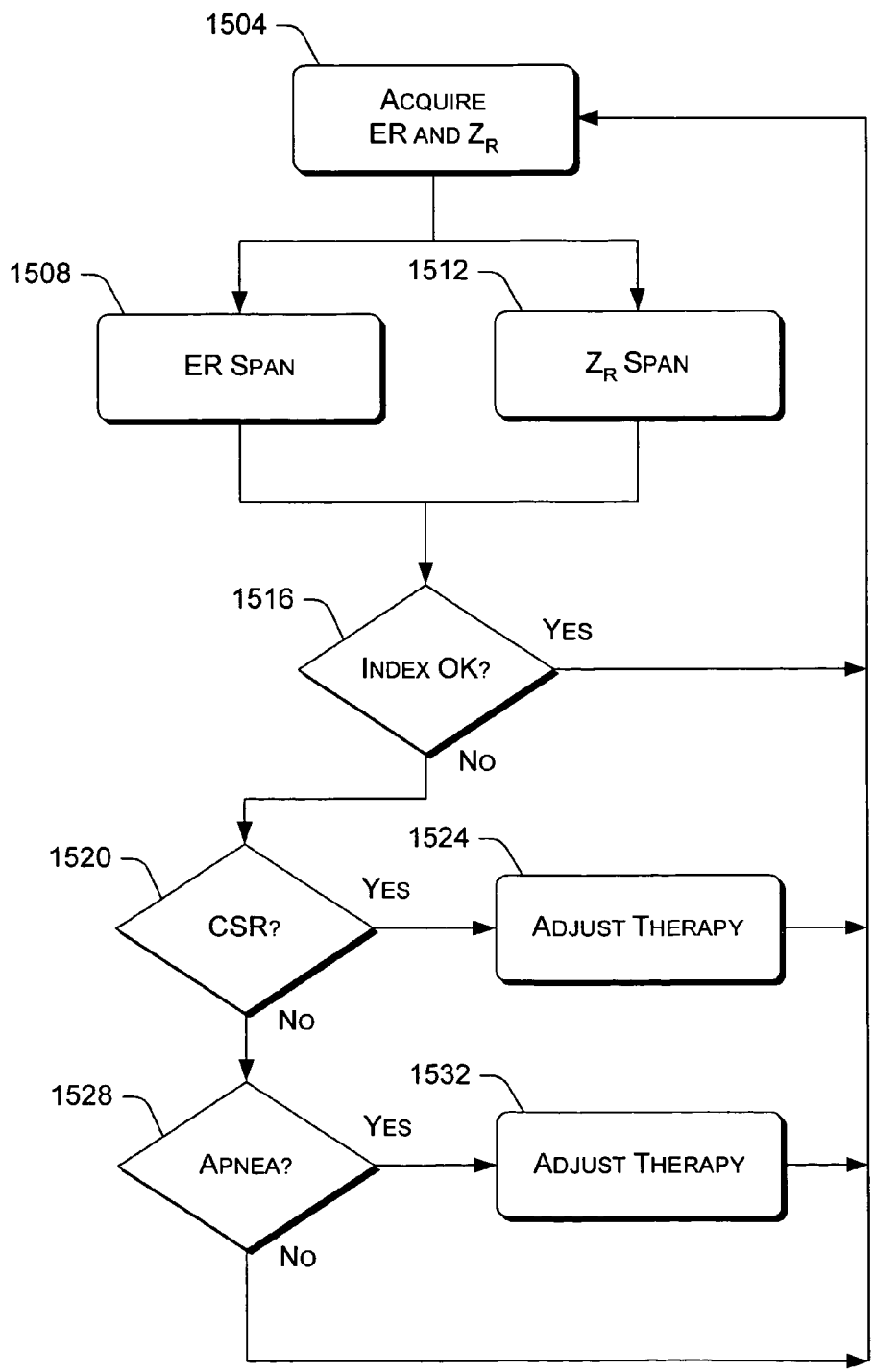
FIG. 15 is a block diagram of an exemplary method that relies at least in part on an evoked response measure span or an impedance measure span to decide if a patient is experiencing or has experienced one or more respiratory issues.

FIG. 15 shows an exemplary method 1500 for adjusting therapy. In an acquisition block 1504, acquisition of evoked response information and impedance information. A ER Span determination block 1508 determines an ER Span value or values based on the acquired information and a $Z_R$ Span determination block 1512 determines a $Z_R$ Span value or values based on the acquired impedance information. A decision block 1516 follows that calculates an index based at least in part on the ER Span and $Z_R$ Span value or values. If the decision block 1516 decides that the index(es) do not indicate a need for adjustment to therapy or that a need, if noted, cannot be adequately addressed or can wait until the patient consults a care provider, the exemplary method 1500 continues at the acquisition block 1504.

If the decision block 1516 decides that the index(es) do not compare favorably to one or more criteria, then the method 1500 continues at an apnea decision block 1520 that decides if the patient is experiencing apnea. If the apnea decision block 1520 decides that the patient is experiencing apnea, then an adjust therapy block 1524 follows that aims to adjust patient therapy to treat apnea. If the apnea decision block 1520 indicates that the patient is not experiencing apnea, then the method 1500 continues at a CSR decision block 1528 that decides if the patient is experiencing CSR. If the patient is experiencing CSR, then an adjust therapy block 1532 follows that aims to adjust patient therapy to treat CSR. If the decision block 1528 decides that the patient is not experiencing CSR, then another decision block may follow, otherwise the method 1500 may continue at the acquisition block 1504. The acquisition block 1504 optionally acquires information regardless of the particular execution task of the method 1500. Further, the exemplary method 1500 optionally acquires patient position information as well.

With respect to therapy adjustment in response to ER Span or $Z_R$ Span information or analysis thereof, therapies are disclosed in copending U.S. patent application Ser. No. 10/968,730, filed Oct. 18, 2004, titled "Tiered Therapy for Respiratory Oscillations Characteristic of Cheyne-Stokes Respiration", incorporated by reference herein. This aforementioned patent application discloses therapies to terminate respiratory issues or to augment respiration. Such therapies optionally include diaphragm activation (e.g., phrenic nerve stimulation, direct diaphragm stimulation, etc.).

As already mentioned, use of span can eliminate a need for baseline or zero-line information. Evoked response or respiration information may be acquired substantially in real time (e.g., via IEGM or impedance acquisition) and adjustments to pacing or other therapy made promptly after a condition or change in condition is detected. Where saturation may be an issue, gain or offset may be adjusted. Various exemplary methods optionally adjust offset in response to a long term average. For example, a running average of impedance (e.g., fixed number of values, forgetting factor, etc.) may used to set adjust offset to help ensure that physiological deviations in impedance above and below are adequately sampled.

Various exemplary methods, devices, systems, etc., use an evoked response PDI to determine patient condition or appropriate therapy. Various exemplary methods, devices, systems, etc., use impedance such as an intrathoracic impedance to determine patient condition or appropriate therapy. Of course, a combination of IEGM information and impedance information may be used for monitoring or selection of therapy. Changes in values over time, based on such information, may be used to determine condition or appropriate therapy. For example, consider a parameter "ΔS", where "S" may be any of a variety of parameters (e.g., ER Span, $Z_R$ Span, number of breaths per unit time, etc.). A daily ΔS value may be determined or another time basis may be used. Of course, use of other bases is possible such as, but not limited to, posture, medication-related, pacing therapy-related, etc.

As already mentioned, impedances may be acquired during sleep or while a patient is awake. Various impedance related parameters may be used to determine condition or therapy, such as, but not limited to, $Z_R$ Span, $Z_{RMin}$, $Z_{RMax}$ or $\Delta Z_R$ Span may be used. In some instances, use of day time impedance information may minimize posture dependence as a patient is generally in a prone position while awake (e.g., sitting or standing). Further, use of a running average of $Z_R$ Span, or other value(s), over day time can minimize posture effects.

An exemplary method uses $Z_R$ Span based on sleep time impedance information and compares a $Z_R$ Span value to an average daytime $Z_R$ Span value to determine whether a condition exists or whether a change in therapy is warranted. Similarly, a $\Delta Z_R$ Span value based on sleep time impedance information may be compared to an average daytime $\Delta Z_R$ Span value, where $\Delta Z_R$ Span reflects breath-to-breath variation. If the sleep time $\Delta Z_R$ Span value fails to meet one or more criteria, then CSR or apnea may be indicated. In the two foregoing examples, the sleep time $Z_R$ Span or $\Delta Z_R$ Span may be used to determine an appropriate therapy. Of course, $\Delta Z_R$ Span and $Z_R$ Span may be used together to determine condition or therapy. For example, apnea is typically characterized by a small $\Delta Z_R$ Span value and a small $Z_R$ Span value whereas a certain phase of CSR may be characterized by progressively diminishing $Z_R$ Span values with a relatively constant $\Delta Z_R$ Span value (see, e.g., the exemplary scenario 1400).

Various exemplary methods, devices, systems, etc., optionally use $Z_{RMin}$ or $Z_{RMax}$ as indicators of condition or selection of therapy. $Z_{RMin}$ or $Z_{RMax}$ may be used in conjunction with $Z_R$ Span or $\Delta Z_R$ Span. For example, absent any significant shift in baseline, $Z_{RMin}$ or $Z_{RMax}$ should decline for as tidal volume declines and increase as tidal volume increases.

While various exemplary methods, devices, systems, etc., include capabilities to monitor patient position (e.g., via an accelerometer), posture testing may be performed and then relevant information communicated to an exemplary implantable device via a programmer. For example, $Z_R$ Span at different postures can be measured and the variation recorded to assist in determining condition or therapy. For example, either a $Z_R$ Span minimum or a mean $Z_R$ Span among all the posture tests (e.g., versus a baseline) can be used to determine a percentage of baseline for use as a criterion.

The exemplary device 100 of FIGS. 1 and 2 is optionally used to implement an exemplary method that includes therapy for prevention and/or treatment of respiratory conditions. Such an exemplary device optionally includes features for diaphragm activation.

CONCLUSION

Although exemplary mechanisms (e.g., implemented as or in methods, devices, systems, software, etc.) have been described in language specific to structural features and/or methodological acts, it is to be understood that the subject matter defined in the appended claims is not necessarily limited to the specific features or acts described.

What is claimed is:

1. A method comprising:
    acquiring impedance values over one or more respiratory cycles;
    determining an impedance span based on the impedance values;
    acquiring IEGMs over one or more respiratory cycles;
    determining evoked response measure values based on the IEGMs;
    determining an evoked response span based on the evoked response measure values;
    based on the impedance span and the evoked response span, determining one or more indexes;
    determining a respiratory condition based on the one or more indexes;
    wherein the respiratory condition is apnea and wherein apnea is characterized by a small impedance span;
    or the respiratory condition is Cheyne-Stokes Respiration (CSR) and wherein CSR is characterized by a progressively diminishing impedance span; and
    adjusting patient therapy if the one or more indexes indicates need for respiratory improvement.

2. The method of claim 1 wherein the impedance span comprises a difference between a minimum impedance value and a maximum impedance value of the acquired impedance values.

3. The method of claim 1 wherein the acquiring comprises acquiring intrathoracic impedance values.

4. The method of claim 1 wherein the acquiring comprises acquiring impedance values using an implantable device.

5. The method of claim 1 wherein patient posture is substantially constant over the one or more respiratory cycles.

6. The method of claim 1 wherein patient activity is substantially constant over the one or more respiratory cycles.

7. The method of claim 1 further comprising determining a cardiac condition based on the one or more indexes and wherein determining the cardiac condition comprises determining whether heart failure exists.

8. The method of claim 7 wherein the determining a cardiac condition determines whether heart failure has worsened.

9. The method of claim 7 wherein the determining a cardiac condition determines whether heart failure has improved.

10. The method of claim 1 wherein the determining a cardiac condition comprises comparing the one or more indexes to a previously determined one or more indexes.

11. The method of claim 1 wherein the evoked response measures comprise post depolarization integrals.

12. The method of claim 1 wherein the evoked response span comprises a difference between a minimum evoked response measure value and a maximum evoked response measure value of the determined evoked response measure values.

13. The method of claim 1 wherein the acquiring comprises acquiring IEGMs using an implantable device.

14. The method of claim 1 wherein patient posture is substantially constant over the one or more respiratory cycles.

15. The method of claim 1 wherein patient activity is substantially constant over the one or more respiratory cycles.

16. The method of claim 1 wherein the determining one or more indexes comprises a product of the impedance span and the evoked response span.

17. The method of claim 1 wherein the determining one or more indexes comprises dividing the evoked response span by the impedance span.

18. A system comprising:
    means for acquiring impedance values over one or more respiratory cycles;
    means for determining an impedance span based on the impedance values;
    means for acquiring IEGMs over one or more respiratory cycles;
    means for determining evoked response measure values based on the IEGMs;
    means for determining an evoked response span based on the evoked response measure values;
    means for determining one or more indexes based on the impedance span and the evoked response span;
    means for determining a respiratory condition based on the one or more indexes;
    wherein the respiratory condition is apnea and wherein apnea is characterized by a small impedance span;
    or the respiratory condition is Cheyne-Stokes Respiration (CSR) and wherein CSR is characterized by a progressively diminishing impedance span; and
    means for adjusting patient therapy if the one or more indexes indicates need for respiratory improvement.

19. The system of claim 18 wherein the means for determining one or more indexes comprises a product of the impedance span and the evoked response span.

20. The system of claim 18 wherein the means for determining one or more indexes comprises dividing the evoked response span by the impedance span.

* * * * *